United States Patent
Shingaya et al.

(10) Patent No.: US 8,601,610 B2
(45) Date of Patent: Dec. 3, 2013

(54) OPTICAL ELECTRIC FIELD ENHANCEMENT ELEMENT AND PROBE USING THE SAME

(75) Inventors: Yoshitaka Shingaya, Ibaraki (JP); Tomonobu Nakayama, Ibaraki (JP); Masakazu Aono, Ibaraki (JP)

(73) Assignees: Japan Science and Technology Agency, Saitama (JP); National Institute for Materials Science, Ibaraki (JP)

( * ) Notice: Subject to any disclaimer, the term of this patent is extended or adjusted under 35 U.S.C. 154(b) by 40 days.

(21) Appl. No.: 12/739,596

(22) PCT Filed: Oct. 24, 2008

(86) PCT No.: PCT/JP2008/069366
§ 371 (c)(1),
(2), (4) Date: Jun. 29, 2010

(87) PCT Pub. No.: WO2009/054507
PCT Pub. Date: Apr. 30, 2009

(65) Prior Publication Data
US 2010/0281587 A1    Nov. 4, 2010

(30) Foreign Application Priority Data

Oct. 24, 2007   (JP) ................................ 2007-276691

(51) Int. Cl.
*G01Q 70/16*     (2010.01)
(52) U.S. Cl.
USPC .................................. 850/60; 850/57; 850/59
(58) Field of Classification Search
USPC ......................................................... 850/60
See application file for complete search history.

(56) References Cited

U.S. PATENT DOCUMENTS

| | | | |
|---|---|---|---|
| 7,073,937 B2* | 7/2006 | Nakayama et al. | 374/164 |
| 7,241,987 B2* | 7/2007 | Saito et al. | 250/234 |
| 2005/0191427 A1* | 9/2005 | Wade et al. | 427/402 |
| 2006/0249384 A1* | 11/2006 | Kim et al. | 204/424 |

OTHER PUBLICATIONS

Katrin Kneipp et al., "Single Molecule Detection Using Surface-Enhanced Raman Scattering (SERS)", Physical Review Letters, vol. 78, No. 9, Mar. 3, 1997, pp. 1667-1670.
Shuming Nie et al., "Probing Single Molecules and Single Nanoparticles by Surface-Enhanced Raman Scattering", Science, vol. 275, Feb. 21, 1997, pp. 1102-1106.
International Search Report mailed Jan. 20, 2009 in International (PCT) Application No. PCT/JP2008/069366.
Yoshitaka Shingaya et al., "Enhancement of Raman scattering with $WO_x$ nanorods", Extended Abstracts, Japan Society of Applied Physics and Related Societies, separate vol. 3, Mar. 27, 2007, p. 1093.
Yoshitaka Shingaya et al., "Epitaxial Growth of $WO_x$ Nanorod on Single Crystal Tungsten Substrate", IEEJ Transactions on Electronics, Information and Systems, Sep. 1, 2007, vol. 127/No. 9, pp. 1320-1323.

* cited by examiner

*Primary Examiner* — Phillip A Johnston
(74) *Attorney, Agent, or Firm* — Wenderoth, Lind & Ponack, L.L.P.

(57) ABSTRACT

An optical electric field enhancement element includes a nanorod which includes a plurality of conductive layers formed therein in a direction parallel to a longitudinal axis of the nanorod. Adjacent conductive layers are isolated from each other via an insulating layer. The nanorod exhibits an effect of enhancing an optical electric field.

12 Claims, 12 Drawing Sheets

OXYGEN-DEFICIENT PLANES  ADSORBED MOLECULE

METAL FINE PARTICLE

MOLECULE $W_5O_{14}$

[0 0 1]

a = 2.33nm b = 2.33nm c = 0.38nm

α, β, γ = 90°

[0 1 0]

⊠ = $WO_6$ unit

500nm

TEM IMAGE
(30nmX30nm)

0.1 M NaCl + 1 nM R6G / H₂O

Ar⁺ Laser 514.5nm, 110μW/μm²    TIME (second)    ELECTRODE POTENTIAL  -100mV vs Ag/AgCl

DOPAMINE MOLECULE

OPTICAL MICROSCOPIC IMAGE
OF TUNGSTEN OXIDE NANORODS
ON Si SUBSTRATE

RAMAN MAPPING OF $^{13}$CO    RAMAN MAPPING OF $^{12}$CO

EXITATION LASER : Ar 514.5 nm, 1.0 mW/μm$^2$

PHOTOIRRADIATION (514.5 nm)

OPTICAL MICROSCOPIC (32μm×25μm)
IMAGE

63μm×49μm

OPTICAL ELECTRIC FIELD ENHANCEMENT ELEMENT AND PROBE USING THE SAME

TECHNICAL FIELD

The present invention relates to an optical electric field enhancement element that enhances an optical electric field, and to a probe using the same.

BACKGROUND ART

For various types of optical elements, means of enhancing the optical electric field have been studied and developed. Means are known which use metal fine particles of gold, silver, copper or the like; however, means capable of attaining enhancement over these have become desired.

DISCLOSURE OF THE INVENTION

Problems that the Invention is to Solve

In consideration of the current situation as described above, an object of the invention is to find out the photoexcitation power enhancement function of a nanorod and to provide an element and a probe using the same.

Means for Solving the Problems

The optical electric field enhancement element of the invention 1 is characterized by comprising a nanorod in which a conductive layer and an insulating layer are laminated.

The optical electric field enhancement element of the invention 2 is characterized in that, in the optical electric field enhancement element of the invention 1, the composition of the nanorod is WOx ($2.5 \leq x \leq 3$).

The probe of the invention 3 is a probe formed of a metal for Raman scattering spectroscopy and is characterized in that one or a large number of the optical electric field enhancement elements of the invention 1 or the invention 2 are formed as standing on the surface of the body thereof.

The probe of the invention 4 is characterized in that, in the probe of the invention 3, the optical electric field enhancement element is a rod-shaped tungsten oxide crystal having a composition of WOx ($2.5 \leq x \leq 3$) and having a diameter of from 10 to 100 nm and a length of from 100 nm to 30 μm.

The probe of the invention 5 is characterized in that, in the probe of the invention 4, the optical electric field enhancement element comprises a WOx nanorod formed by filling an ultra-high vacuum chamber with oxygen under a pressure of from $5 \times 10^{-7}$ to $5 \times 10^{-5}$ Torr, heating a tungsten foil at $10 \times 10^2$ to $13 \times 10^{2\circ}$ C. under the condition to thereby sublime tungsten oxide, then making the tungsten oxide deposited on the body formed of tungsten and heated at $6 \times 10^2$ to $8 \times 10^{2\circ}$ C., and growing it to stand thereon.

The probe of the invention 6 is characterized in that, in the probe of the invention 3, the optical electric field enhancement element comprises a tungsten oxide nanorod capable of exhibiting a high Raman scattering enhancement effect as having a {001} crystallographic shear structure in the crystal and having a nano-gap structure where the conductive planes on an atomic layer level are isolated from each other via an insulating layer.

The probe of the invention 7 is characterized in that, in the probe of the invention 3, the optical electric field enhancement element is formed through local oxidation of a tungsten oxide nanorod by laser irradiation in air, and this exhibits a Raman scattering enhancement effect of at least $10^{10}$, therefore enabling detection of single-molecule Raman scattering.

The probe of the invention 8 is characterized in that, in the probe of the invention 3, the optical electric field enhancement element is formed through local reduction of a tungsten oxide nanorod by heating in the presence of carbon or carbon monoxide, and this exhibits a Raman scattering enhancement effect of at least $10^{10}$, therefore enabling detection of single-molecule Raman scattering.

The probe of the invention 9 is characterized in that, in the probe of the invention 3, it enables detection of molecules existing in a thin concentration of at most 1 nM in an aqueous solution, owing to the Raman scattering enhancement effect of the tungsten oxide nanorod therein.

The probe of the invention 10 is characterized in that, in the probe of the invention 3, it enables detection of molecular vibration of single molecules in an aqueous solution, owing to the Raman scattering enhancement effect of the tungsten oxide nanorod therein.

The probe of the invention 11 is characterized in that, in the probe of the invention 3, it may be incorporated in a microscopic Raman spectroscopic device by arranging the tip part of the tungsten oxide nanorod at the focal position of the objective lens.

The probe of the invention 12 is characterized in that, in the probe of the invention 3, it may be incorporated in a scanning probe microscope by fusing the tungsten oxide nanorod with the probe tip of the scanning probe microscope by laser irradiation in such a state that one nanorod is kept standing at the probe tip.

The probe of the invention 13 is characterized in that, in the probe of the invention 3, it may induce local chemical reaction by exciting the molecules existing in the vicinity of the tungsten oxide nanorod by light or heat through photoirradiation of the nanorod.

EFFECT OF THE INVENTION

The optical electric field enhancement element of the invention can realize high-level optical electric field amplification heretofore unknown in the art, by itself or by bonding it to a mother body.

Arranging the optical electric field enhancement element to stand on a surface through crystal growth thereon makes it possible to unify the nanogap distance, therefore bringing about the effect of Raman scattering enhancement stably for a long period of time. The gap distance is determined at the time of crystal growth, and therefore the gap distance can be controlled by the growth condition.

Further, the probe using the optical electric field enhancement element greatly enhances Raman scattering spectroscopy, therefore enabling various high-precision analyses heretofore impossible in the art.

BEST MODE FOR CARRYING OUT THE INVENTION

Embodiments of the optical electric field enhancement element of the invention are described in detail hereinunder.

The present inventors have found that a tungsten oxide nanorod has an optical electric field enhancement effect; and applying this having the effect to various base materials, the inventors have succeeded in greatly improving the function of the materials. In this description, "nanorod" is meant to indicate a rod-shaped crystal having a diameter of from 10 to 100 nm and a length of from 100 nm to 30 μm.

The optical electric field enhancement element of the invention is an element for enhancing an optical electric field, and is composed of a conductive layer and an insulating layer that are laminated therein. In the following, an optical electric field enhancement element composed of a tungsten oxide nanorod is described primarily.

Figure 1:
FIG. 1 is a schematic view showing the structure of a tungsten oxide nanorod.

FIG. 1 is a schematic view showing the structure of a tungsten oxide nanorod. As shown in FIG. 1, a tungsten oxide nanorod has oxygen-deficient planes formed therein in the direction parallel to the long axis of the rod. The oxygen-deficient planes are conductive planes each having a thickness on an atomic level. The adjacent conductive planes are isolated from each other via an insulator ($WO_3$) having a thickness of a few nm, and it is considered that the nano-size layered structure could significantly contribute toward enhancing an optical electric field. This may be presumed from the effect of metal fine particles of gold, silver, copper or the like mentioned below heretofore well known in the art.

Figure 2:
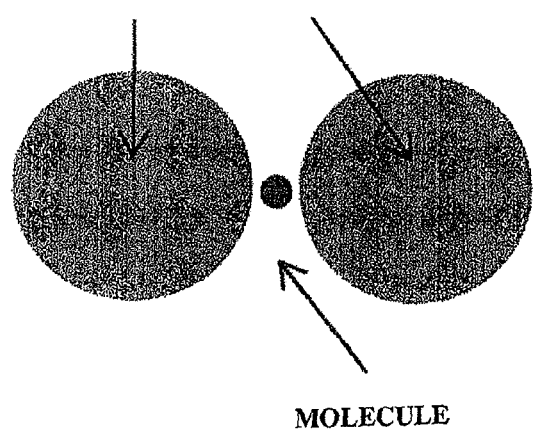
FIG. 2 is a schematic view showing a conventional technology of enhanced Raman scattering.

Localized surface plasmons exist on nanometer-scale metal fine particles; and by exciting the surface plasmons through photoirradiation, an extremely enhanced localized electromagnetic field is formed on the surfaces of metal fine particles. Owing to the effect of the enhanced electromagnetic field, the Raman scattering intensity of the molecules adsorbed by the surfaces of metal fine particles is extremely enhanced. In ordinary Raman scattering spectroscopy, minor molecules could not be detected since the scattering cross sections thereof are on a level of $10^{30}$ $cm^2$/molecule and are extremely small. However, surface-enhanced Raman scattering with metal fine particles of gold, silver, copper or the like brings about an extremely great enhancing effect of from $10^{10}$ to $10^{15}$, therefore enabling detection of single-molecule Raman scattering. It is known that an especially great enhancing effect is given to the nanogap area between the fine particles in an aggregation of plural metal fine particles. FIG. 2 shows a schematic view of a conventional technology of enhanced Raman scattering (metal fine particles).

Heretofore, those capable of giving electric field enhancement that enables single-molecule-level enhanced Raman scattering spectroscopy were limited to fine particles of gold and silver. In addition, single-molecule Raman spectroscopy could be realized only in the nanogap formed by aggregation of fine particles.

In the invention, the crystal structure itself of a tungsten oxide nanorod includes a structure where conductive planes are isolated from an insulating layer, and therefore, a nanogap exists inside the crystal structure. Owing to this structure, an extremely large electric field enhancement effect is expected, and single-molecule Raman spectroscopy has been realized actually using a tungsten oxide nanorod.

In an intermediate oxide of tungsten, the value x varies within a range of from 2 to 3. In a bulk crystal, the composition could be controlled by controlling the oxygen partial pressure and the annealing temperature; however, composition control is difficult in fine crystals such as nanorods. In fact, tungsten oxide nanorods of various compositions have been reported.

Figure 3:
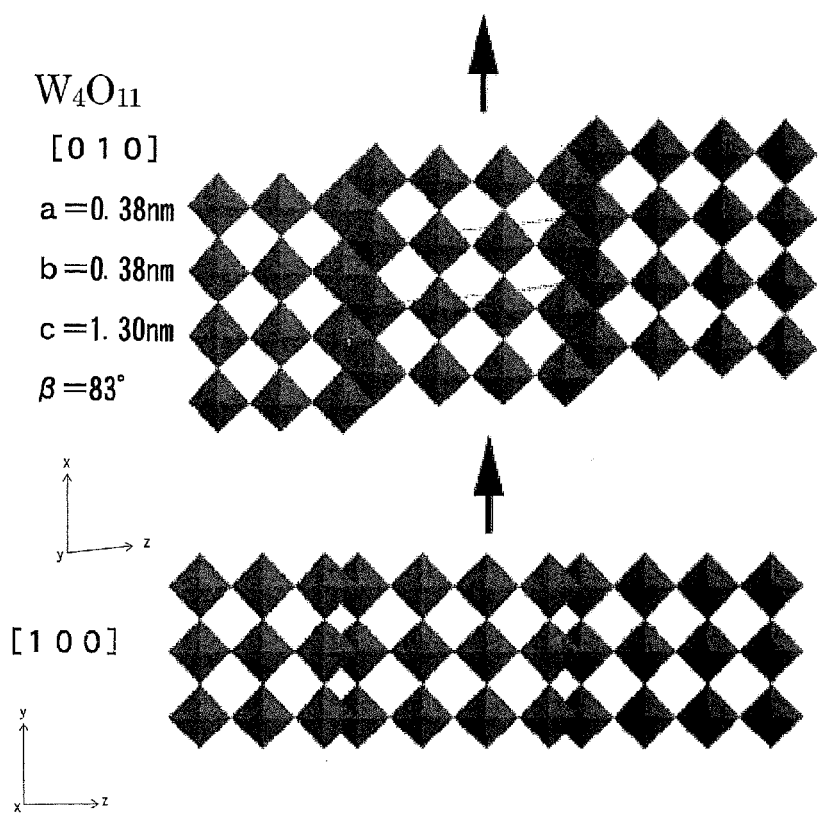
FIG. 3 is a schematic view showing the crystal structure of a $W_4O_{11}$ tungsten oxide nanorod.
Figure 4:
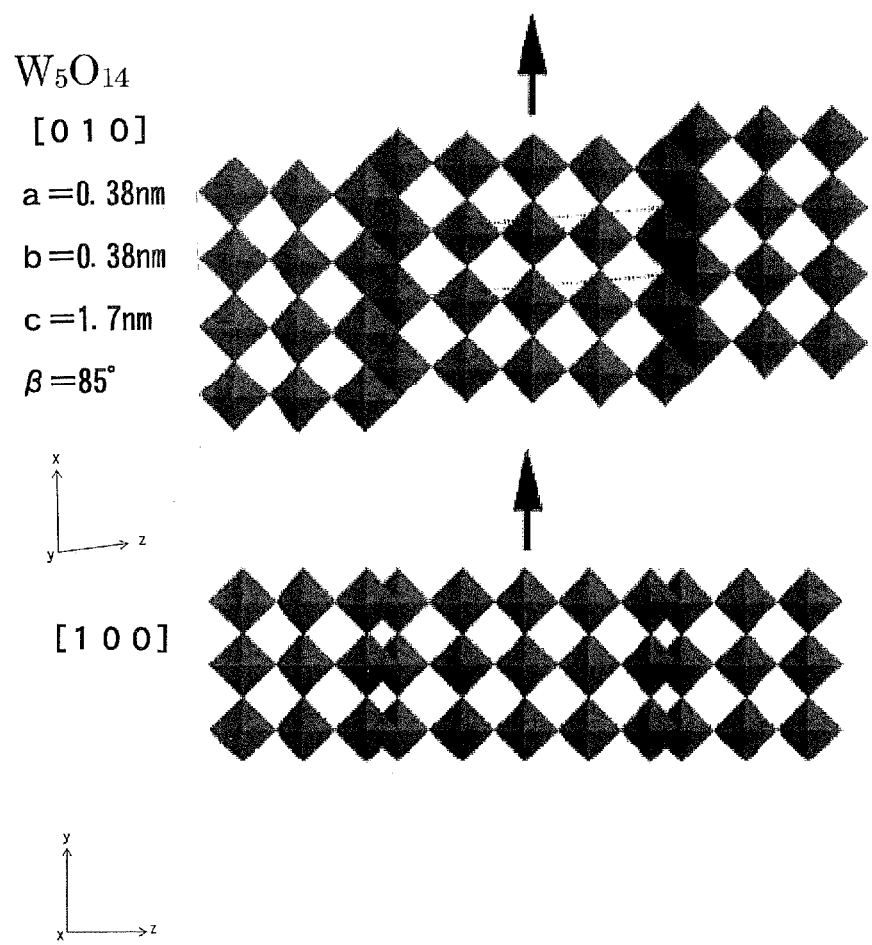
FIG. 4 is a schematic view showing the crystal structure of a $W_5O_{14}$ tungsten oxide nanorod.

It is considered that the structure capable of especially remarkably exhibiting the optical electric field enhancement effect this time would be a {001} CS (crystallographic shear—the same shall apply hereinunder) structure of FIG. 3 and FIG. 4. FIG. 3 is a schematic view showing the crystal structure of a $W_4O_{11}$ tungsten oxide nanorod; and FIG. 4 is a schematic view showing the crystal structure of a $W_5O_{14}$ tungsten oxide nanorod. In this CS structure, there forms a shear structure owing to the oxygen defects inside the crystal. A general formula of the {001} CS structure is $W_nO_{3n-1}$ (where n is an integer), in which the smallest n is 2. Chemical formulae corresponding to n=2, 3, 4, 5 and 6 are $W_2O_5=WO_{2.5}$, $W_3O_8=WO_{2.67}$, $W_4O_{11}=WO_{2.75}$, $W_5O_{14}=WO_{2.8}$, $W_6O_{17}=WO_{2.83}$, which indicate the existence of a deficient plane at every n-th row.

A further larger n value is available; and one nanorod may have various n values as mixed therein. Accordingly, the value x in WOx may almost continuously vary within a range of from 2.5 to 3.

Figure 5:
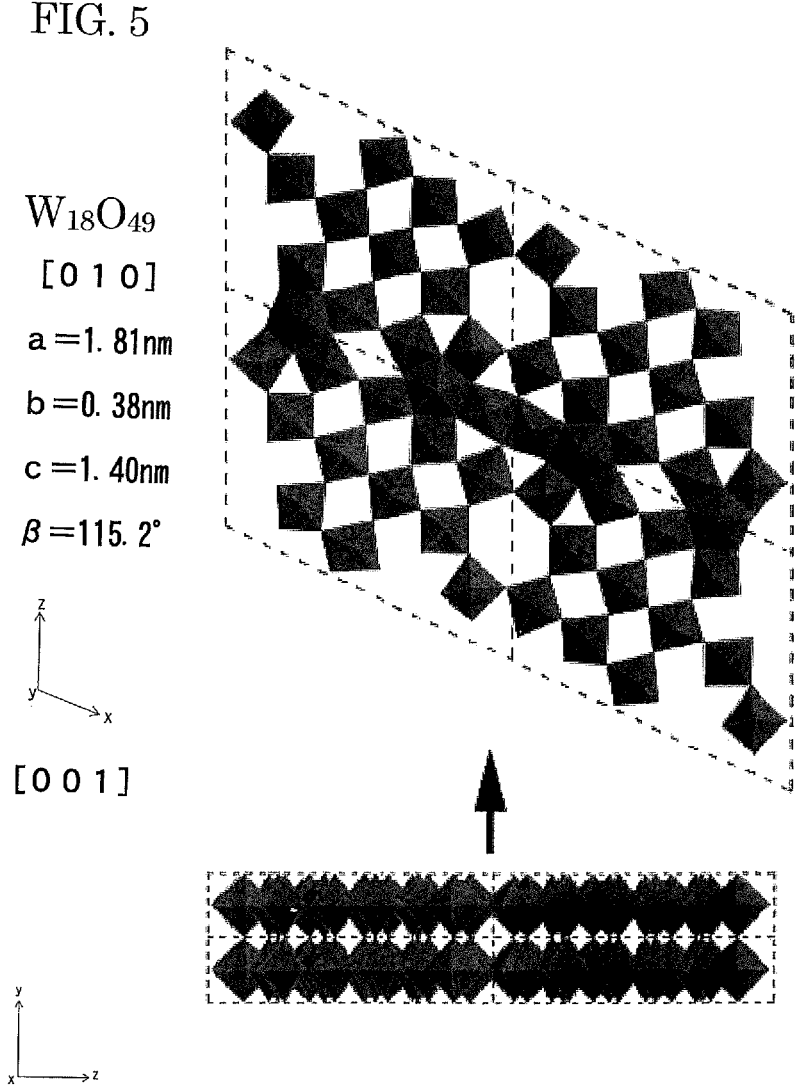
FIG. 5 is a schematic view showing the crystal structure of a $W_{18}O_{49}$ tungsten oxide nanorod.

Contrary to this, the tungsten oxide nanorod structure of $W_{18}O_{49}=WO_{2.72}$ shown in FIG. 5 has a more complicated network structure. This $W_{18}O_{49}$ is called γ-tungsten oxide, and is one of stable intermediate oxides. Though not having a {001} CS structure, this oxide is also considered to have an optical electric field enhancement effect, as it is conductive.

Figure 6:
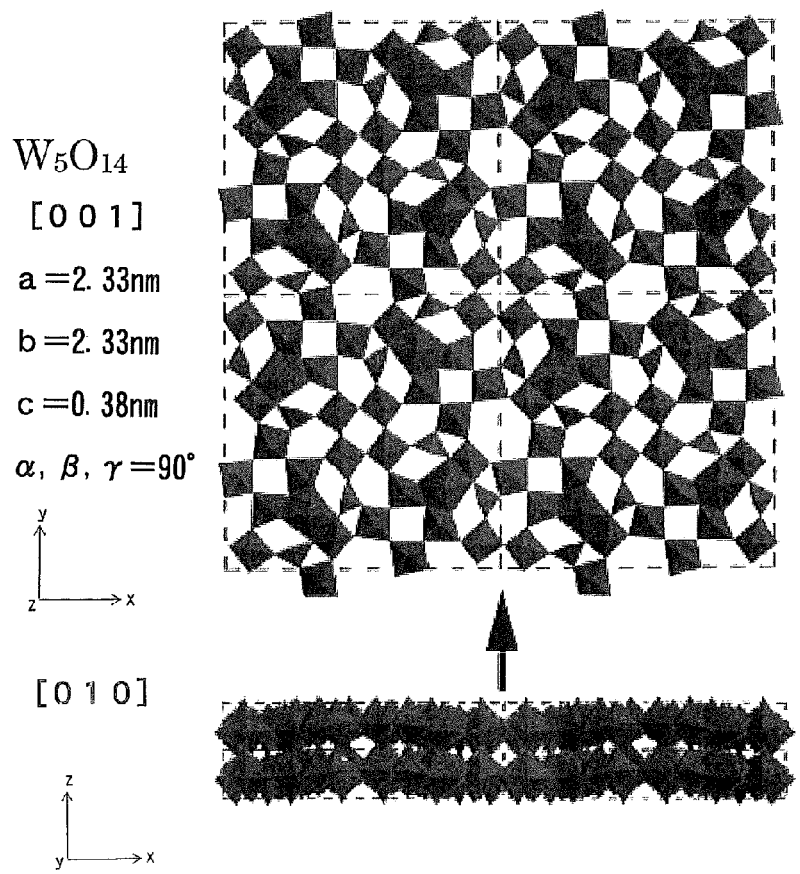
FIG. 6 is a schematic view showing the crystal structure of a $W_5O_{14}$ tungsten oxide nanorod.

Regarding the $W_5O_{14}$ tungsten oxide nanorod having the network structure of FIG. 6, this structure is also considered to have an optical electric field enhancement effect though there are no data relating to the conductivity thereof.

Figure 7:
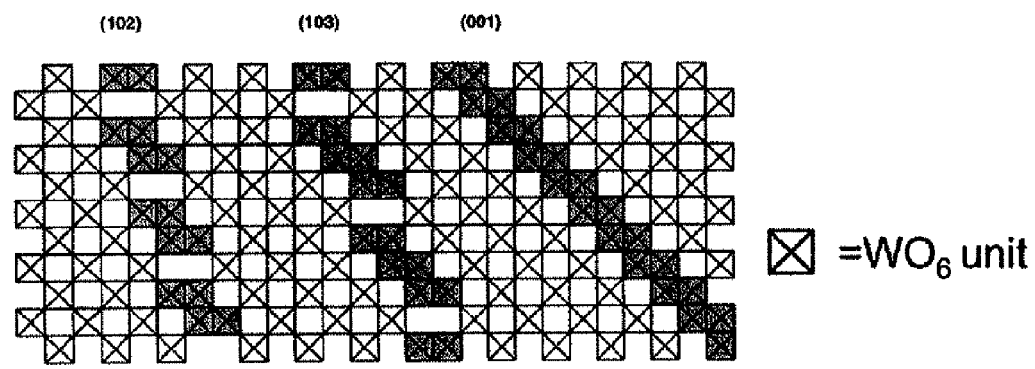
FIG. 7 is a schematic view of the CS structure of tungsten oxide.

Of bulk crystals, it is known that those having a small amount of oxygen defects, or that is, those having a larger value x may have a structure with oxygen-deficient planes introduced in different directions from those in the {001} CS structure, or that is, a {102} CS structure or a {103} CS structure. The {102} CS structure appears in the crystals where x is within a range of from 2.93 to 2.98. The {103} CS structure appears in those where x is within a range of from 2.87 to 2.93. Regarding the electroconductivity of these cases, the {102} CS structure is semiconductive, and the {103} CS structure is metallic; however, the two both have a high resistivity. Accordingly, it is considered that the {102} CS structure and the {103} CS structure could not have a so high electric field enhancement effect. FIG. 7 is a schematic view of the CS structure of tungsten oxide.

Next described is a probe comprising the optical electric field enhancement element of the invention.

The probe of the invention comprises a metal for use for Raman scattering spectroscopy, and is so designed that one or more (a large number) of the above-mentioned optical electric field enhancement elements are held to stand on the surface of the body of the probe. Hereinunder primarily described is an embodiment where the optical electric field enhancement element is a tungsten oxide nanorod.

A tungsten oxide nanorod may be grown on the tip of a sharp-pointed metal probe. The active site of enhanced Raman spectroscopy exists at the tip of a nanorod, and therefore, this is kept adjacent to the surface of a solid in scanning. In that manner, the information of the molecules existing on the surface could be obtained at a space resolution over the light diffraction limit that could not be attained in a light scanning method. Enhanced Raman scattering with a probe is realized by the use of a probe of gold or silver; however, the enhancement capable of realizing single-molecule Raman scattering could not be obtained. It is difficult to fit an aggregate of fine particles to the tip of a probe with its structure kept as such, and this is not realized. The probe with a tungsten oxide nanorod of the invention makes it possible to realize the single-molecule Raman scattering.

Figure 8:
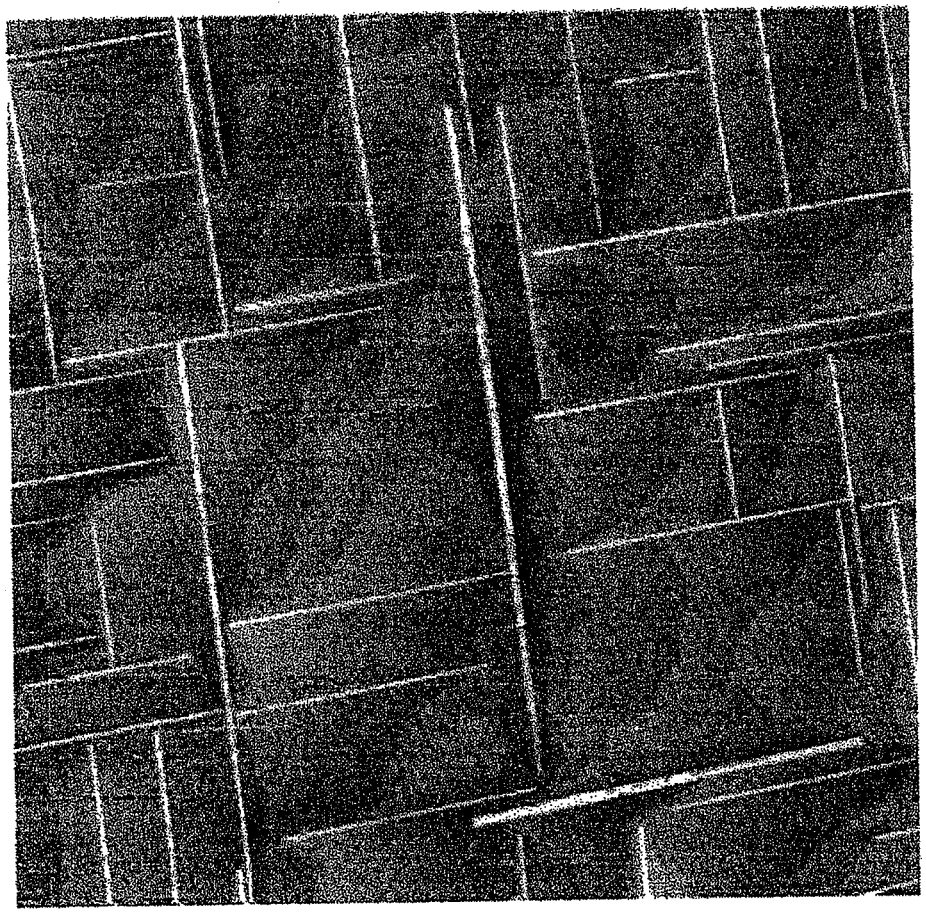
FIG. 8 is a view of a scanning tunnel microscope image (1 μm×1 μm) of nanowires on an Si substrate formed with a tungsten oxide nanorod probe.

It has already been confirmed that a tungsten oxide nanorod can be used as a probe for an actual scanning probe microscope; and FIG. 8 shows a scanning tunnel microscope image (1 µm×1 µm) of nanowires on an Si substrate formed with a tungsten oxide nanorod (diameter 20 nm, length 300 nm) serving as a probe.

Figure 9:
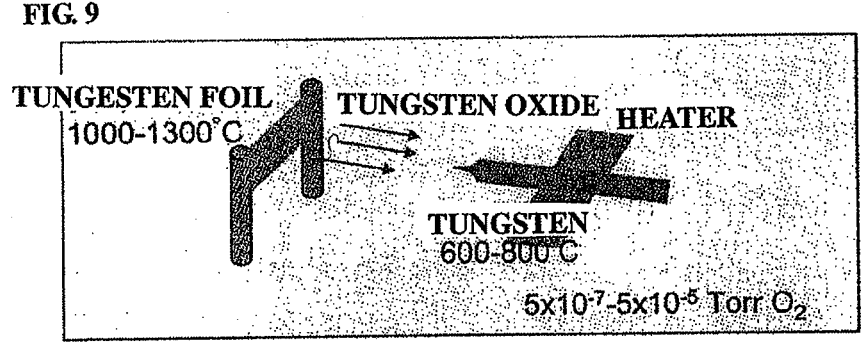
FIG. 9 is a schematic view of a method for forming a tungsten oxide nanorod.
Figure 10:
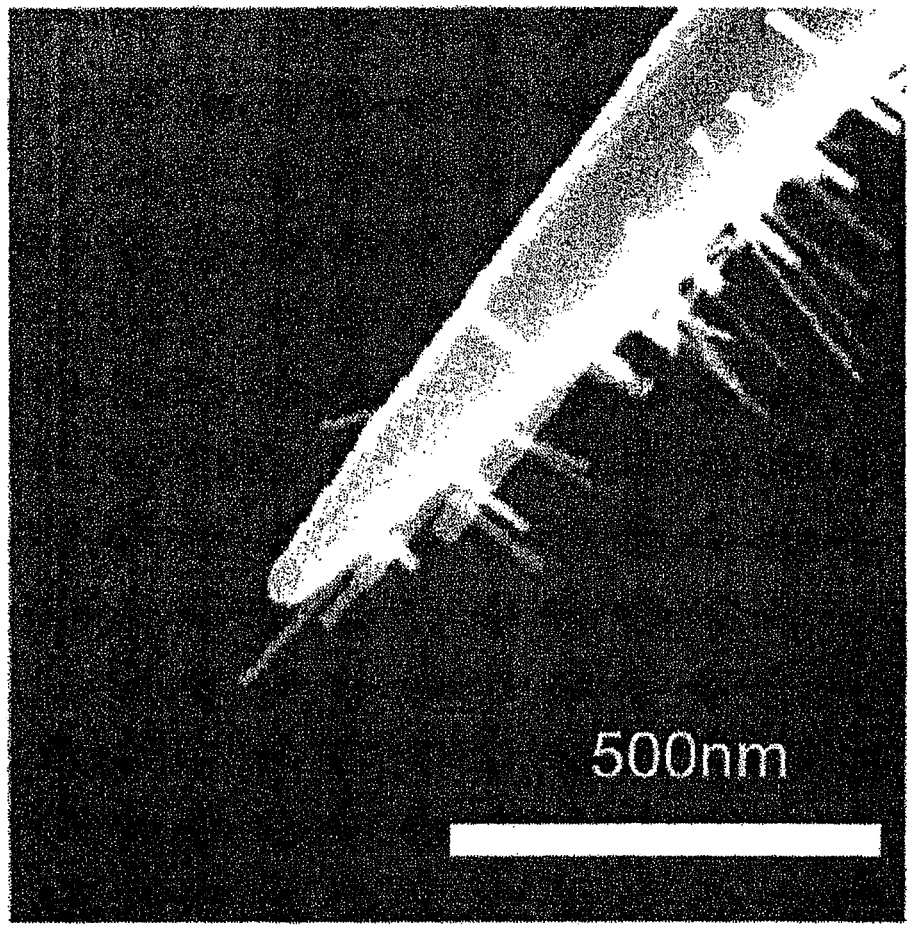
FIG. 10 is a view of a SEM image of a tungsten oxide nanorod growing at the tip of a metal probe.
Figure 11:
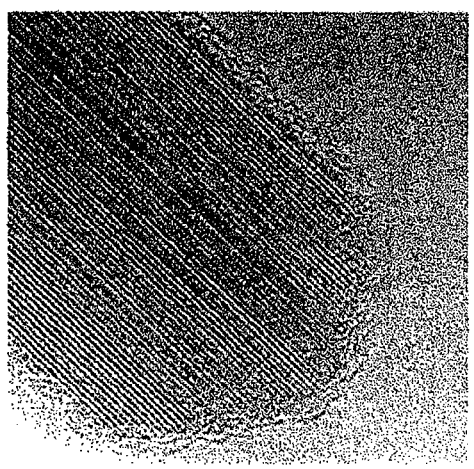
FIG. 11 is a TEM photograph sowing the tip of a tungsten oxide nanorod of the invention.

The tungsten oxide nanorod for use for the probe of the invention can be formed according to the forming method schematically shown in FIG. 9. As the substrate, for example, used is tungsten of which the tip is sharpened according to an electrolytic polishing method. On the tungsten, tungsten oxide is vapor-deposited from a tungsten foil, and is grown thereon. An ultra-high-vacuum chamber is filled with oxygen under a pressure falling within a range of from $5 \times 10^{-7}$ to $5 \times 10^{-5}$ Torr, and under the condition, the tungsten foil is heated at 1000 to 1300° C. and tungsten oxide is thereby sublimed from it. The tungsten oxide is vapor-deposited on the tungsten heated at 600 to 800° C., and a WOx nanorod is thereby grown on it. The WOx nanorod epitaxially grows relative to the substrate tungsten. In a conventional nanorod forming method, the epitaxial growth is not employed and the value x of the formed WOx nanorod varies in a wide range. In the present growing method, the growth is epitaxial, and the method is clean as using an ultra-high-vacuum chamber; and therefore, WOx nanorods having a relatively uniform composition can be formed. FIG. 10 shows a scanning electron microscopic (SEM) image of a tungsten oxide nanorod growing at the tip of a metal probe. FIG. 11 shows a transmission electron microscopic (TEM) image showing the tip of a tungsten oxide nanorod of the invention.

Next described are applications for the probe of the invention. In all applications, WOx nanorods having a {001} CS structure (x=2.5 to 3) are employable. Within a visible light range, they exhibit an enhancement effect at any wavelength. In particular, they exhibit a high enhancement effect at around 500 nm, but it is considered that the peak wavelength could be adjusted by controlling the structure of the nanorods.

[Single-Molecule Detection with Fluorescent Microscope]

As a method of single-molecule detection, there is known a fluorescent microscopic method using a dye molecule, which, however, requires pre-marking with a dye molecule. The method has some problems in that long-term observation is difficult owing to fading of the dye molecule, and a position resolution over a light diffraction limit is unavailable. Enhanced Raman scattering spectroscopy with a sensor comprising the tungsten oxide nanorod of the invention enables single-molecule detection that solves the problems, and in addition, it may provide detailed information relating to the environment in which the molecule exists.

[Molecular Discrimination Probe (Sensor)]

The extremely large optical electric field enhancement effect of a tungsten oxide nanorod provides a single-molecule Raman spectrum. The Raman spectrum clarifies the molecular structure, therefore enabling the identification and the discrimination of infinitesimal molecules existing at the tip of the probe. Scanning the probe enables mapping of minor molecules. A tungsten oxide nanorod is stable in an aqueous solution and in an organic solvent, therefore providing a three-dimensional distribution of minor molecules on an atomic/molecular scale at an extremely high space resolution. In fact, minor rhodamine 6G molecules existing in an aqueous solution on an nM level could be discriminated from the Raman spectrum thereof. The applicability of the probe to an extremely wide range may be taken into consideration. For example, in a biological field, the probe is applicable to identification of minor proteins and biosignal transmitters, decoding of DNA base sequences, clarification of substance transport process in living cells, etc. In a chemical field, the probe is applicable to clarification of local active sites in catalytic reaction, clarification of reaction mechanism by identification of reaction intermediates, clarification of electrode surfaces in fuel cells, etc.

Figure 12:
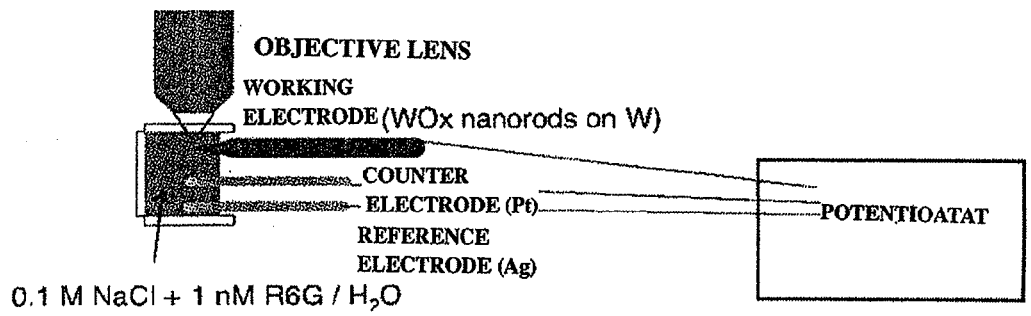
FIG. 12 is a schematic view of a setup for observing the absorption/desorption of molecules in an aqueous electrolytic solution by enhanced Raman with a nanorod probe.

As shown in FIG. 12, the tungsten tip with a tungsten oxide nanorod growing thereon was immersed in an aqueous electrolytic solution to be a working electrode therein. In this, a platinum wire was arranged as a counter electrode and a silver wire as a reference electrode, one nanorod growing on the tip was irradiated with laser light with electrochemically controlling the potential of the working electrode, and the Raman scattering was observed. The nanorod used here was previously irradiated with laser at a wavelength of 514.5 nm and at an intensity of 0.5 mW/µm² in air so that it could attain a large Raman scattering enhancement effect especially at around the tip of the nanorod.

Figure 13:
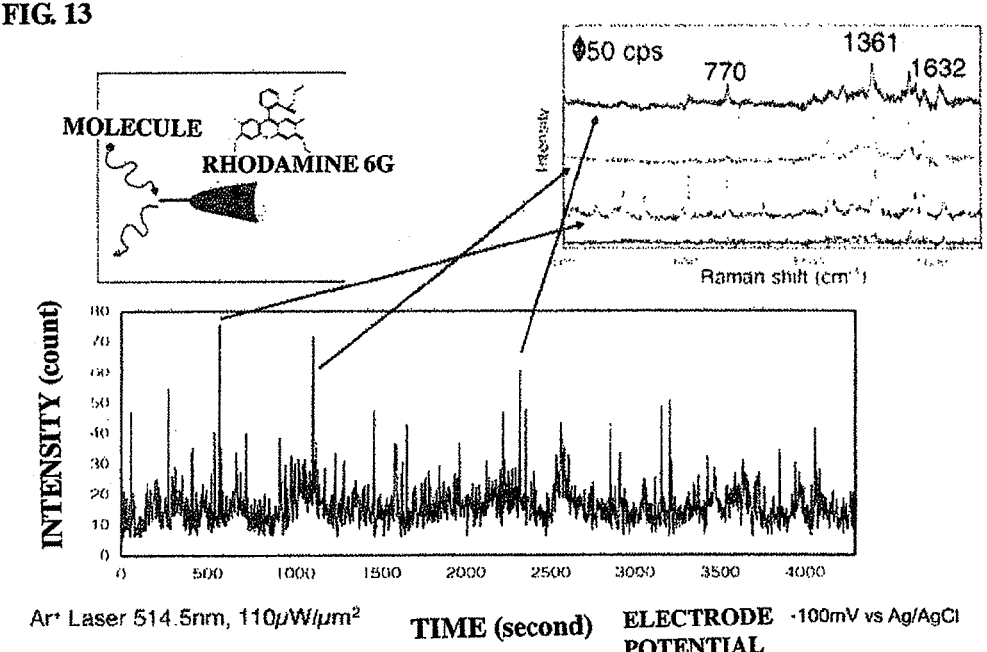
FIG. 13 is a view in observation of blinking through absorption/desorption of rhodamine 6G molecules in an aqueous electrolytic solution.

As shown in FIG. 12, an extremely minor amount, 1 nM of rhodamine 6G molecules exist in the electrolytic solution. The potential of the working electrode is −100 mV vs Ag/AgCl, at which the single-molecule adsorption/desorption of rhodamine 6G molecules is observed as blinking. In FIG. 13, the peak intensity at around 1360 cm$^{-1}$ is plotted as a function of time. The peaks appearing in the lower graph in FIG. 13 are by single-molecule adsorption by the WOx nanorod. The spectrum of rhodamine 6G molecules at each peak in the lower graph in FIG. 13 gave different peak intensity ratios and wavenumbers every time, and this result confirms the observation of single-molecule-level adsorption/desorption.

Figure 14:
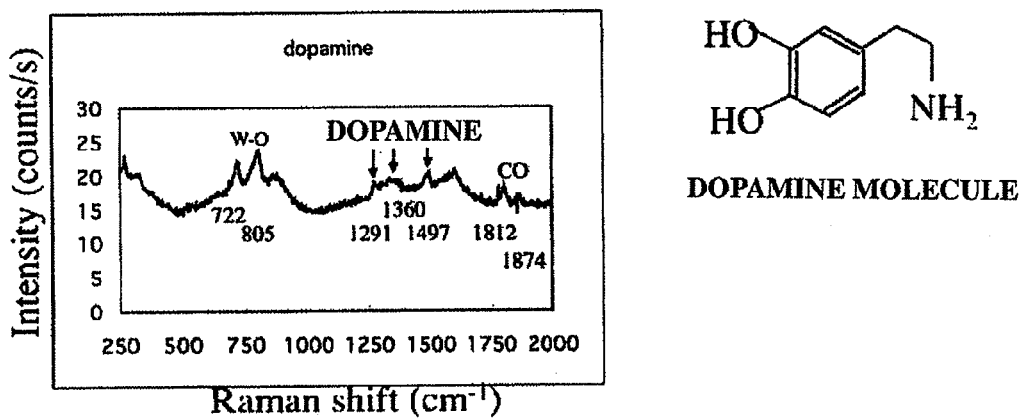
FIG. 14 is a view showing a Raman spectrum of a dopamine molecule on a tungsten oxide nanorod.

On the other hand, a dopamine molecule is a type of molecules used for information transmission at the synapse of nerve cells. A slightly-oxidized tungsten oxide nanorod was immersed in an aqueous solution of 0.1 M NaCl+50 μM dopamine for Raman scattering spectroscopy at the nanorod tip. The actual experiment arrangement is the same as that in blinking observation of rhodamine 6G molecules. As in FIG. 14, peaks derived from the dopamine adsorbed by the surface of the nanorod are seen.

[Isotope Discrimination Probe]

Figure 15:
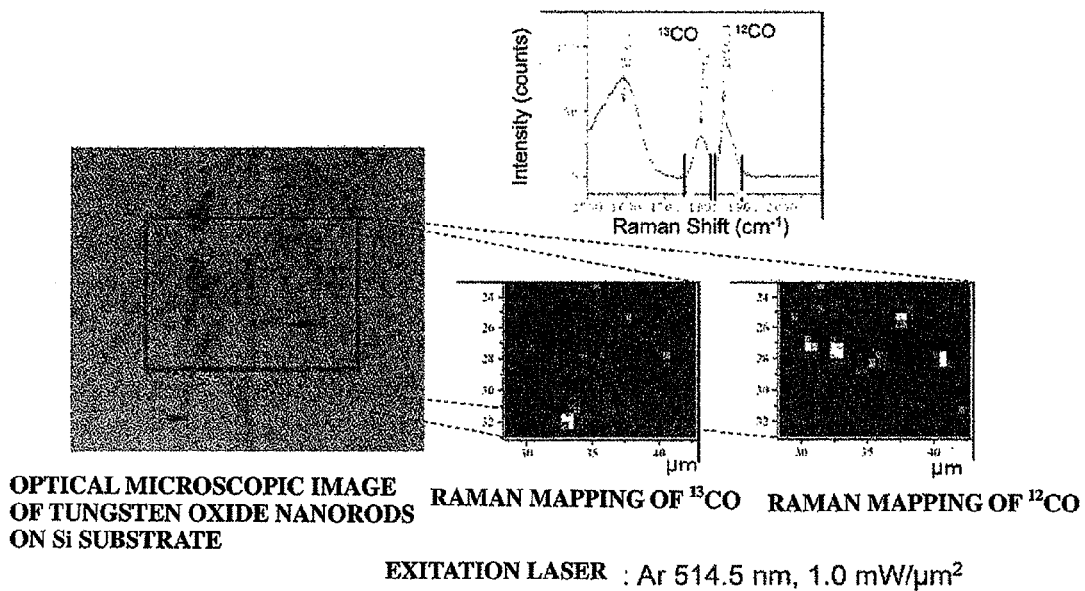
FIG. 15 is a view showing Raman mapping of adsorbed CO (single-molecule level CO detection).
Figure 16:
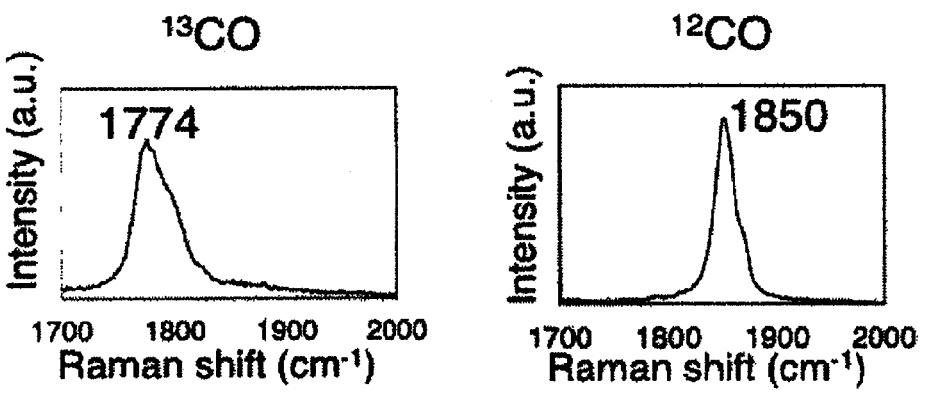
FIG. 16 is a view showing the Raman scattering spectrum of adsorbed $^{13}CO$ and adsorbed $^{12}CO$.
Figure 17:
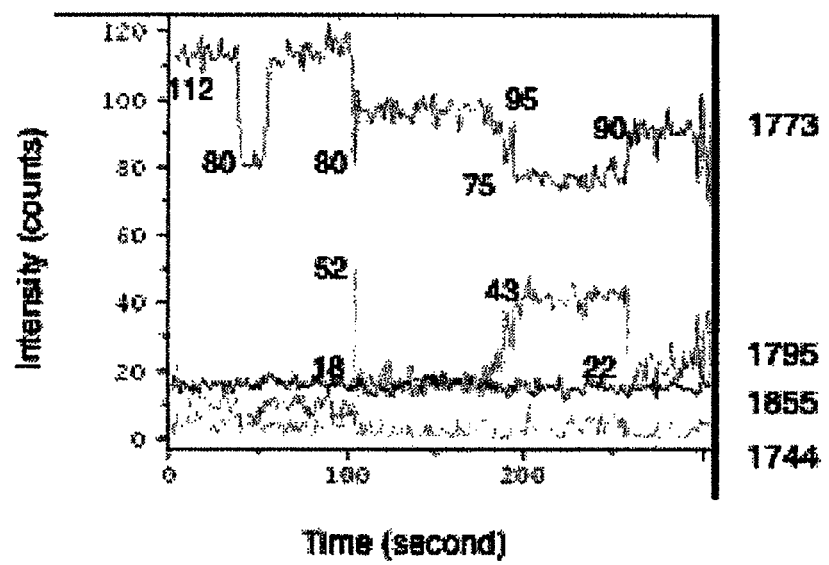
FIG. 17 is a graph showing the time dependence of the peak intensity of adsorbed CO molecules (showing blinking).

Of conventional gold or silver fine particles, only one nanogap exist between the fine particles; however, the nanorod may have a structure in which nanogaps are laminated, and therefore this may provide Raman scattering enhancement larger than before. Heretofore, the molecules that enable single-molecule Raman scattering spectroscopy are limited to dye molecules that have a large Raman scattering cross section owing to the resonance effect of the molecules of themselves; however, though a tungsten oxide nanorod is a carbon monoxide molecule that is not a dye molecule, the present inventors have succeeded in single-molecule Raman detection using the tungsten oxide nanorod. FIG. 15 shows an explanatory view of Raman mapping of adsorbed CO (single-molecule level CO detection). In fact, using carbon isotopes, when $^{12}CO$ and $^{13}CO$ were adsorbed by tungsten oxide nanorods in a ratio of 1/1, any one isotope was observed at one enhanced Raman active site; and therefore this verifies the single-molecule level detectability. FIG. 16 shows the Raman scattering spectrum of adsorbed $^{13}CO$ and adsorbed $^{12}CO$. In that manner, Raman spectroscopy is vibration spectroscopy, in which, therefore, isotopic elements having a different mass can be discriminated by the frequency of vibration thereof. Use of the probe enables age determination of minor samples. In addition, the blinking of CO molecules was also observed. FIG. 17 shows the time dependence of the peak intensity of adsorbed CO molecules. The blinking means a phenomenon that the peak intensity and the wavenumber vary with time, and this is taken as the direct evidence for single-molecule Raman spectroscopy. The nanorod exhibiting such an especially remarkable electric field enhancement that enables such single-molecule detection can be realized by slightly oxidizing or reducing a grown nanorod. Local oxidation of tungsten oxide nanorods can be attained by irradiation with laser light at a narrowed spot diameter of 1 μm and at an intensity of from 0.1 mW/μm$^2$ to 10 mW/μm$^2$ in air.

[Local Chemical Reaction Inducing Element]

By irradiation of a tungsten oxide nanorod with light, the molecules existing in the vicinity of the nanorod may be excited by light or heat, thereby locally inducing chemical reaction. In fact, there is an experimental result indicating local formation of amorphous carbon by photoirradiation of nanorods in an oil. Applications include local chemical reaction induction in living cells, local cell destruction therein, and medical treatment for cancer.

Figure 18:
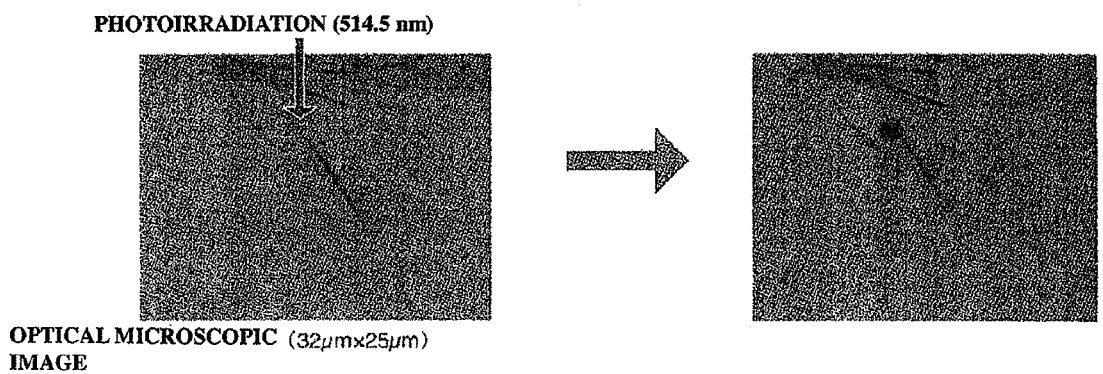
FIG. 18 is a view of an optical microscopic image before and after local reaction induction by nanorod.
Figure 19:
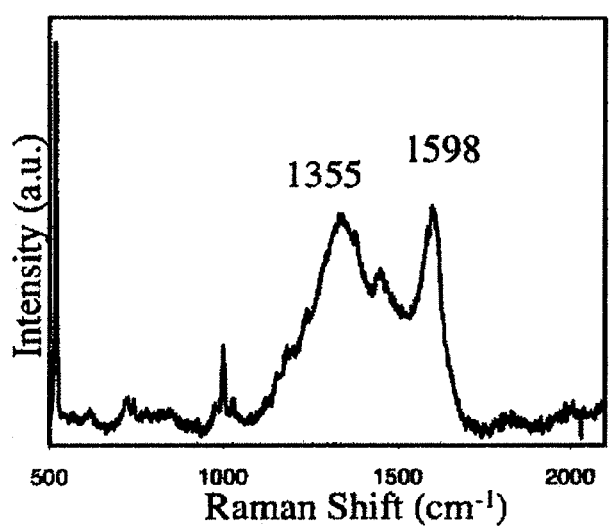
FIG. 19 is a view showing the Raman scattering spectrum of amorphous carbon formed through local reaction induction by nanorod.

In an oil (polybutene 60%, diarylalkane 40%), the tip of a tungsten oxide nanorod is irradiated with laser at a spot diameter of 1 μm and at an intensity of 0.8 mW (514.5 nm), which gives a dark spot (right-hand view) in the optical microscopic image (FIG. 18). The spot is analyzed for the Raman scattering spectrum, which gives peaks characteristic of amorphous carbon as in FIG. 19. This indicates the decomposition of the molecules constituting the oil by light or heat. The region where the nanorod does not exist is irradiated with light at the same intensity; in this, however, no reaction occurs. Accordingly, it is understood that the decomposition of the organic molecules is induced by the tungsten oxide nanorod.

A tungsten oxide nanorod grown on a tungsten tip was kept in contact with a silicon substrate under optical microscopic observation, mechanically cut by applying force thereto, and dispersed on the silicon substrate. Using a 100-power oil immersion objective lens, the nanorod kept immersed in the oil was observed to give the optical microscopic image (FIG. 18).

[Use as Photocatalyst]

Figure 20:
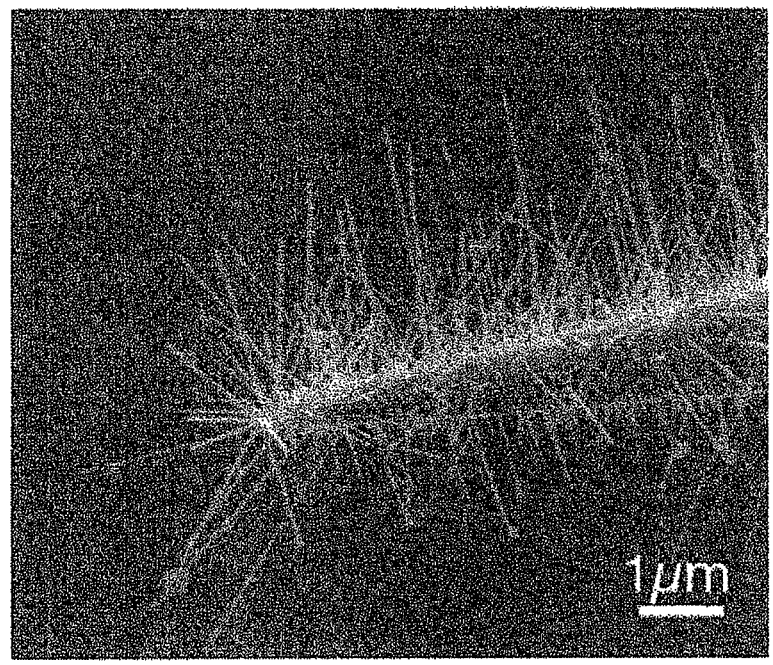
FIG. 20 is a view of a SEM image showing adhesion of spherical amorphous carbon to a tungsten oxide nanorod.
Figure 21:
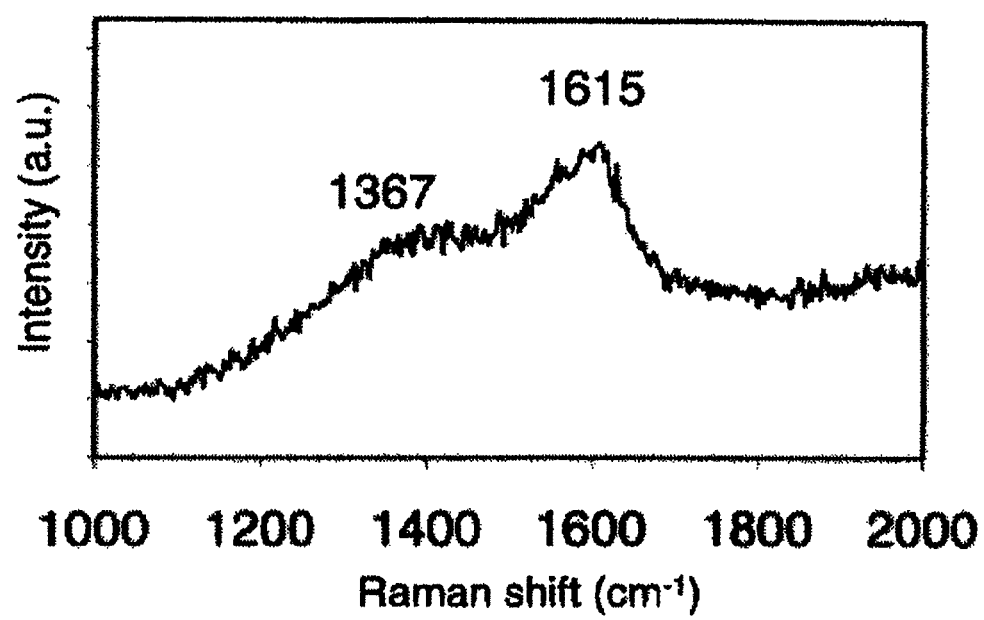
FIG. 21 is a view showing the Raman scattering spectrum of amorphous carbon adhering to a tungsten oxide nanorod.

A tungsten oxide nanorod has a catalytic activity in the surface thereof. As in the SEM image in FIG. 20, amorphous carbon forms on the surface of a tungsten oxide nanorod in air. The spherical substance adhering to the nanorod is amorphous carbon. FIG. 21 shows a Raman scattering spectrum indicating that the adhering substance is amorphous carbon. It is considered that this may be formed by decomposition of organic molecules in air. The formation of amorphous carbon is promoted by photoirradiation, and a tungsten oxide rod can be used as a photocatalyst in a visible light region.

[Fixation to Atomic Force Microscope Tip]

Figure 22:
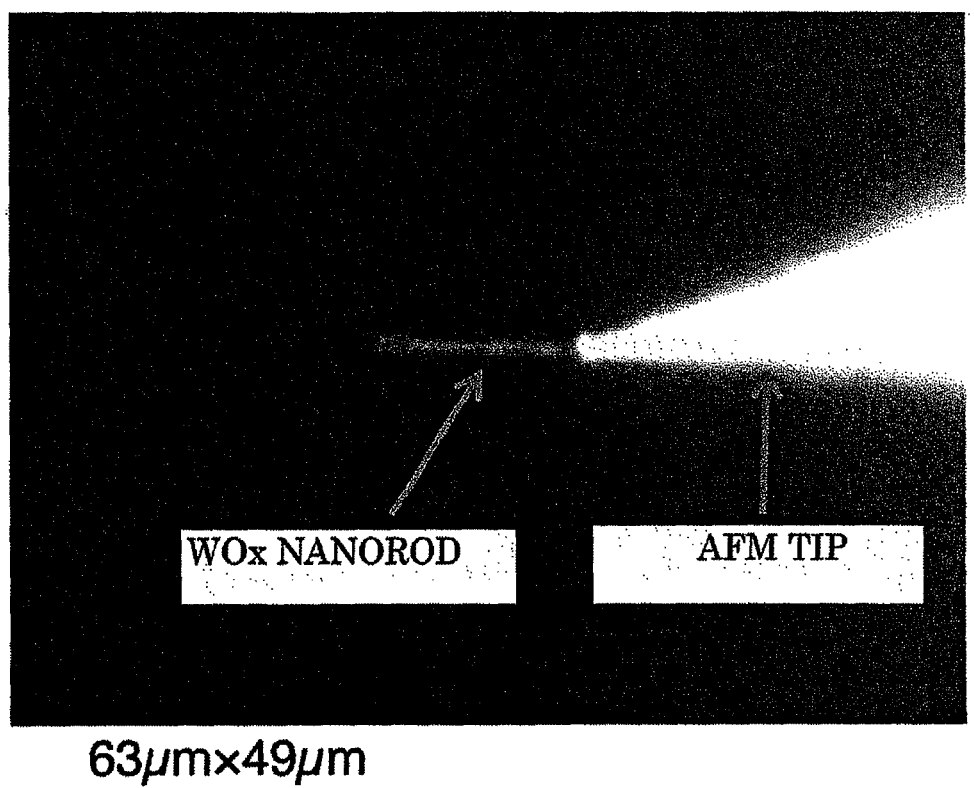
FIG. 22 is a view of an optical microscopic image of an atomic force microscope tip with one tungsten oxide nanorod alone fitted to the tip.

For use as a local molecule probe, it is important to use a tungsten oxide nanorod probe as the probe for an atomic force microscope. One of a large number of tungsten oxide nanorods grown on a tungsten substrate is contacted with the tip of an atomic force microscope (AFM) using a fine-focus stage under optical microscopic observation. Next, as in FIG. 22, the contact point between the nanorod and the tip is irradiated with laser, whereby the nanorod is fixed to the tip.

EXAMPLES

Next described are Examples of the invention.

Example 1

As the substrate, used was a tungsten polycrystalline wire of which the tip had been sharpened according to an electrolytic polishing method and of which the basal part had a thickness of 0.25 mm and a length of 20 mm. In the setup schematically shown in FIG. 9, the ultra-high-vacuum chamber was filled with oxygen under a pressure of $6 \times 10^{-6}$ Torr, and under the condition, a tungsten foil (thickness 0.02 mm: evaporation source) was heated at 1250° C. and tungsten oxide was thereby sublimed. The tungsten oxide was vapor-deposited on the tungsten substrate heated at 730° C., and grown into a WOx nanorod for a growth period of time of 10 hours.

A method of determining the value x of the intermediate oxides except normal compositions such as $WO_2$, $WO_3$ and the like, from the Raman spectrum is not established. Therefore, utilizing the fact that the peaks of the Raman spectrum of tungsten oxide appear at different wavenumbers in accordance with the value of x, the value was estimated based on the peaks (the same shall apply hereinunder). The length and the diameter of the tungsten oxide nanorods shown below are the mean values of the obtained nanorods.

The WOx nanorods formed in the above were annealed at 780° C. for 30 minutes for ordering of the oxygen-deficient planes (process 1-1). The value x of the WOx nanorods was from 2.6 to 2.9, the length thereof was 4 μm, and the diameter thereof was 50 nm.

Next, the WOx nanorods were analyzed for the Raman scattering enhancement degree. The Raman scattering enhancement degree was determined according to the above-mentioned method using rhodamine 6G (R in Table 1), from the intensity ratio at the peak given by the bulk crystal and the peak given by the single-layer adsorbed species (the same shall apply hereinunder). As a result, the Raman scattering enhancement degree was $2 \times 10^4$.

Further, the WOx nanorods were analyzed for the applicability thereof to the following applications mentioned above.

(1) Molecular discrimination probe (sensitivity on a single layer level).

(2) Molecular discrimination probe (sensitivity for single molecule).

(3) Isotopic discrimination probe (sensitivity on a single layer level).

(4) Isotopic discrimination probe (sensitivity for single molecule).

(5) Local chemical reaction induction probe.

(6) Efficiency increase in photocatalyst.

As a result, it has been confirmed that the WOx nanorods are applicable to (1), (3), (5) and (6).

Table 1 shows the experimental results of the samples formed in Examples; and Table 2 shows the results in using the samples of Examples.

TABLE 1

| | | Condition for WOx vapor deposition | | | | WOx nanorods | | |
|---|---|---|---|---|---|---|---|---|
| | Substrate | Oxygen Pressure (Torr) | Heating Temperature for Vapor Deposition Source (°C.) | Heating Temperature For Substrate (°C.) | Growing Time (hours) | Estimated Value x | Length (μm) | Diameter (nm) |
| Example 1 | polycrystalline | $6 \times 10^{-6}$ | 1250 | 730 | 10 | 2.6-2.9 | 4 | 50 |
| Example 2 | polycrystalline | $6 \times 10^{-6}$ | 1250 | 730 | 10 | 2.6-2.9 | 4 | 50 |
| Example 3 | polycrystalline | $6 \times 10^{-6}$ | 1250 | 730 | 10 | 2.6-2.9 | 4 | 50 |
| Example 4 | single-crystalline | $6 \times 10^{-6}$ | 1250 | 730 | 10 | 2.6-2.9 | 2 | 30 |
| Example 5 | single-crystalline | $6 \times 10^{-6}$ | 1200 | 730 | 10 | 2.6-2.9 | 4 | 50 |
| Example 6 | polycrystalline | $6 \times 10^{-6}$ | 1200 | 730 | 10 | 2.6-2.9 | 4 | 50 |
| Example 7 | polycrystalline | $6 \times 10^{-6}$ | 1200 | 730 | 10 | 2.6-2.9 | 4 | 50 |
| Example 8 | polycrystalline | $6 \times 10^{-6}$ | 1200 | 730 | 10 | 2.6-2.9 | 4 | 50 |
| Example 9 | polycrystalline | $7 \times 10^{-6}$ | 1200 | 730 | 10 | 2.6-2.9 | 5 | 50 |
| Example 10 | polycrystalline | $7 \times 10^{-6}$ | 1200 | 730 | 10 | 2.6-2.9 | 5 | 50 |
| Example 11 | polycrystalline | $7 \times 10^{-6}$ | 1110 | 730 | 10 | 2.6-2.9 | 4 | 50 |
| Example 12 | polycrystalline | $7 \times 10^{-6}$ | 1110 | 730 | 20 | 2.6-2.9 | 5 | 50 |
| Example 13 | polycrystalline | $7 \times 10^{-6}$ | 1120 | 730 | 20 | 2.6-2.9 | 5 | 50 |
| Example 14 | polycrystalline | $7 \times 10^{-6}$ | 1120 | 730-850 | 20 | 2.6-2.9 | 10 | 75 |
| Example 15 | polycrystalline | $6 \times 10^{-6}$ | 1100 | 730-850 | 20 | 2.6-2.9 | 10 | 75 |
| Example 16 | polycrystalline | $6 \times 10^{-6}$ | 1100 | 730-850 | 20 | 2.6-2.9 | 10 | 75 |
| Example 17 | polycrystalline | $5 \times 10^{-6}$ | 1100 | 730-850 | 5 | 2.6-2.9 | 3 | 30 |
| Example 18 | polycrystalline | $5 \times 10^{-6}$ | 1100 | 730-850 | 5 | 2.6-2.9 | 3 | 30 |
| Example 19 | polycrystalline | $5 \times 10^{-6}$ | 1100 | 730-850 | 5 | 2.6-2.9 | 3 | 40 |
| Example 20 | polycrystalline | $5 \times 10^{-6}$ | 1100 | 730-850 | 5 | 2.6-2.9 | 4 | 50 |
| Example 21 | polycrystalline | $5 \times 10^{-6}$ | 1100 | 730-850 | 5 | 2.6-2.9 | 4 | 50 |
| Example 22 | polycrystalline | $5 \times 10^{-6}$ | 1130 | 730-850 | 5 | 2.6-2.9 | 2 | 30 |
| Example 23 | polycrystalline | $5 \times 10^{-6}$ | 1200 | 730-850 | 5 | 2.6-2.9 | 2 | 30 |
| Example 24 | polycrystalline | $5 \times 10^{-6}$ | 1200 | 730-850 | 5 | 2.6-2.9 | 3 | 30 |
| Example 25 | polycrystalline | $5 \times 10^{-6}$ | 1250 | 730-850 | 5 | 2.6-2.9 | 4 | 40 |
| Example 26 | polycrystalline | $5 \times 10^{-6}$ | 1250 | 730-850 | 5 | 2.6-2.9 | 4 | 40 |
| Example 27 | polycrystalline | $5 \times 10^{-6}$ | 1250 | 730-850 | 5 | 2.6-2.9 | 4 | 40 |
| Comparative Example | polycrystalline | | | | | | | |

TABLE 2

| | Process | Raman Scattering Enhancement Degree | Applicability to Applications | | | | | |
|---|---|---|---|---|---|---|---|---|
| | | | (1) | (2) | (3) | (4) | (5) | (6) |
| Example 1 | (process 1-1) | $2 \times 10^4$ (R) | ○ | | ○ | | ○ | ○ |
| Example 2 | (process 1-1) & (process 2) | $1 \times 10^4$ (R) | ○ | | ○ | | ○ | ○ |
| Example 3 | — | | ○ | | ○ | | ○ | ○ |
| Example 4 | — | | ○ | | ○ | | ○ | ○ |
| Example 5 | — | | ○ | | ○ | | ○ | ○ |
| Example 6 | (process 1-2) | | ○ | | ○ | | ○ | ○ |
| Example 7 | (process 3) | | ○ | | ○ | | ○ | ○ |
| Example 8 | (process 1-1) | | ○ | | ○ | | ○ | ○ |
| Example 9 | (process 1-1) & (process 2) | $1 \times 10^4$ (R) | ○ | | ○ | | ○ | ○ |
| Example 10 | — | | ○ | | ○ | | ○ | ○ |

TABLE 2-continued

| | Process | Raman Scattering Enhancement Degree | (1) | (2) | (3) | (4) | (5) | (6) |
|---|---|---|---|---|---|---|---|---|
| Example 11 | — | | ○ | ○ | | | ○ | ○ |
| Example 12 | — | | ○ | ○ | | | ○ | ○ |
| Example 13 | (process 1-2) | | ○ | ○ | | | ○ | ○ |
| Example 14 | — | | ○ | ○ | | | ○ | ○ |
| Example 15 | (process 2) | $1 \times 10^3$ (R) | ○ | ○ | | | ○ | ○ |
| Example 16 | — | | ○ | ○ | | | ○ | ○ |
| Example 17 | (process 4) | $1 \times 10^{10}$ (R) ≤ (C) | ○ | ○ | ○ | ○ | ○ | ○ |
| Example 18 | (process 5) | $1 \times 10^{10}$ (R) ≤ (C) | ○ | ○ | ○ | ○ | ○ | ○ |
| Example 19 | (process 6) | $1 \times 10^{10}$ (R) ≤ (C) | ○ | ○ | ○ | ○ | ○ | ○ |
| Example 20 | — | | ○ | ○ | | | ○ | ○ |
| Example 21 | (process 5) | $1 \times 10^{10}$ (R) ≤ (C) | ○ | ○ | ○ | ○ | ○ | ○ |
| Example 22 | — | | ○ | ○ | | | ○ | ○ |
| Example 23 | — | | ○ | ○ | | | ○ | ○ |
| Example 24 | (process 5) | $1 \times 10^{10}$ (R) ≤ (C) | ○ | ○ | ○ | ○ | ○ | ○ |
| Example 25 | — | | ○ | ○ | | | ○ | ○ |
| Example 26 | (process 5) | $1 \times 10^{10}$ (R) ≤ (C) | ○ | ○ | ○ | ○ | ○ | ○ |
| Example 27 | (process 7) | $1 \times 10^{10}$ (R) ≤ (C) | ○ | ○ | ○ | ○ | ○ | ○ |
| Comparative Example | — | | X | X | X | X | X | X |

Example 2

WOx nanorods were formed in the same manner as in Example 1. In addition to the above process 1-1 given thereto, these WOx nanorods were sulfidized at 780° C. for 20 minutes under a pressure of $5 \times 10^{-5}$ Torr ($H_2S$) for forming a $WS_2$ film on the surfaces of the WOx nanorods for the purpose of inhibiting the reactivity of the surfaces of the WOx nanorods (process 2). The value x and the dimension of the WOx nanorods were the same as those in Example 1.

The WOx nanorods were analyzed for the Raman scattering enhancement degree thereof in the same manner as in Example 1. As a result, the degree was $1 \times 10^4$. Further, the WOx nanorods were analyzed for the applicability thereof to the above-mentioned applications, and the same results as in Example 1 were obtained.

Example 3

WOx nanorods were formed in the same manner as in Example 1. These nanorods were not processed as in the above. The value x and the dimension of the WOx nanorods were the same as those in Example 1. The WOx nanorods were analyzed for the applicability thereof to the above-mentioned applications, and the same results as in Example 1 were obtained.

Example 4

WOx nanorods were formed in the same manner as in Example 1, for which, however, a single-crystalline (110) substrate (in Table 1, this is expressed as "single-crystalline") was used. These nanorods were not processed as in the above. The value x of the WOx nanorods was the same as in Example 1; and they had a length of 2 μm and a diameter of 30 nm. The WOx nanorods were analyzed for the applicability thereof to the above-mentioned applications, and the same results as in Example 1 were obtained.

Example 5

WOx nanorods were formed in the same manner as in Example 1, for which, however, a single-crystalline (110) was used, and the heating temperature for the tungsten foil was 1200° C. These nanorods were not processed as in the above. The value x and the dimension of the WOx nanorods were the same as in Example 1. The WOx nanorods were analyzed for the applicability thereof to the above-mentioned applications, and the same results as in Example 1 were obtained.

Example 6

WOx nanorods were formed in the same manner as in Example 1, for which, however, the heating temperature for the tungsten foil was 1200° C. These nanorods were annealed at 850° C. for 60 minutes for ordering of the oxygen-deficient planes (process 1-2). The value x and the dimension of the WOx nanorods were the same as in Example 1. The WOx nanorods were analyzed for the applicability thereof to the above-mentioned applications, and the same results as in Example 1 were obtained.

Example 7

WOx nanorods were formed in the same manner as in Example 1, for which, however, the heating temperature for the tungsten foil was 1200° C. These nanorods were reduced with hydrogen ($D_2$) under a pressure of $10^{-3}$ Torr for 60 minutes (process 3). The value x and the dimension of the WOx nanorods were the same as in Example 1. The WOx nanorods were analyzed for the applicability thereof to the above-mentioned applications, and the same results as in Example 1 were obtained.

Example 8

WOx nanorods were formed in the same manner as in Example 1, for which, however, the heating temperature for the tungsten foil was 1200° C. These nanorods were processed according to the above process 1-1. The value x and the dimension of the WOx nanorods were the same as in Example 1. The WOx nanorods were analyzed for the applicability thereof to the above-mentioned applications, and the same results as in Example 1 were obtained.

Example 9

WOx nanorods were formed in the same manner as in Example 1, for which, however, the oxygen pressure was $7\times10^{-6}$ Torr and the heating temperature for the tungsten foil was 1200° C. These nanorods were processed according to the above process 1-1 and process 2. The value x and the diameter of the WOx nanorods were the same as in Example 1; and the length thereof was 5 µm. The WOx nanorods were analyzed for the Raman scattering enhancement degree in the same manner as in Example 1. As a result, the degree was $1\times10^4$. Further, the WOx nanorods were analyzed for the applicability thereof to the above-mentioned applications, and the same results as in Example 1 were obtained.

Example 10

WOx nanorods were formed in the same manner as in Example 1, for which, however, the oxygen pressure was $7\times10^{-6}$ Torr and the heating temperature for the tungsten foil was 1200° C. These nanorods were not processed as in the above. The value x and the diameter of the WOx nanorods were the same as in Example 1; and the length thereof was 5 µm. The WOx nanorods were analyzed for the applicability thereof to the above-mentioned applications, and the same results as in Example 1 were obtained.

Example 11

WOx nanorods were formed in the same manner as in Example 1, for which, however, the oxygen pressure was $7\times10^{-6}$ and the heating temperature for the tungsten foil was 1110° C. These nanorods were not processed as in the above. The value x and the dimension of the WOx nanorods were the same as in Example 1. The WOx nanorods were analyzed for the applicability thereof to the above-mentioned applications, and the same results as in Example 1 were obtained.

Example 12

WOx nanorods were formed in the same manner as in Example 1, for which, however, the oxygen pressure was $7\times10^{-6}$ Torr, the heating temperature for the tungsten foil was 1110° C., and the growth time was 20 hours. These nanorods were not processed as in the above. The value x and the diameter of the WOx nanorods were the same as in Example 1; and the length thereof was 5 µm. The WOx nanorods were analyzed for the applicability thereof to the above-mentioned applications, and the same results as in Example 1 were obtained.

Example 13

WOx nanorods were formed in the same manner as in Example 1, for which, however, the oxygen pressure was $7\times10^{-6}$ Torr, the heating temperature for the tungsten foil was 1120° C., and the growth time was 20 hours. These WOx nanorods were processed according to the process 1-2. The value x and the diameter of the WOx nanorods were the same as in Example 1; and the length thereof was 5 µm. The WOx nanorods were analyzed for the applicability thereof to the above-mentioned applications, and the same results as in Example 1 were obtained.

Example 14

WOx nanorods were formed in the same manner as in Example 1, for which, however, the oxygen pressure was $7\times10^{-6}$ Torr, the heating temperature for the tungsten foil was 1120° C., the substrate temperature was 730° C. at first and 850° C. at the end and was elevated proportionately during this, and the growth time was 20 hours. These WOx nanorods were not processed as in the above. The value x of the WOx nanorods was the same as in Example 1; the length thereof was 10 µm; and the diameter thereof was 75 nm. The WOx nanorods were analyzed for the applicability thereof to the above-mentioned applications, and the same results as in Example 1 were obtained.

Example 15

WOx nanorods were formed in the same manner as in Example 1, for which, however, the oxygen pressure was $5\times10^{-6}$ Torr, the heating temperature for the tungsten foil was 1110° C., the substrate temperature was 730° C. at first and 850° C. at the end and was elevated proportionately during this, and the growth time was 20 hours. These WOx nanorods were processed according to the process 2. The value x of the WOx nanorods was the same as in Example 1; the length thereof was 10 µm; and the diameter thereof was 75 nm. The WOx nanorods were analyzed for the Raman scattering enhancement degree in the same manner as in Example 1, and was $1\times10^3$. The WOx nanorods were analyzed for the applicability thereof to the above-mentioned applications, and the same results as in Example 1 were obtained.

Example 16

WOx nanorods were formed in the same manner as in Example 1, for which, however, the oxygen pressure was $5\times10^{-6}$ Torr, the heating temperature for the tungsten foil was 1100° C., the substrate temperature was 730° C. at first and 850° C. at the end and was elevated proportionately during this, and the growth time was 20 hours. These WOx nanorods were not processed as in the above. The value x of the WOx nanorods was the same as in Example 1; the length thereof was 10 µm; and the diameter thereof was 75 nm. The WOx nanorods were analyzed for the applicability thereof to the above-mentioned applications, and the same results as in Example 1 were obtained.

Example 17

WOx nanorods were formed in the same manner as in Example 1, for which, however, the oxygen pressure was $5 \times 10^{-6}$ Torr, the heating temperature for the tungsten foil was 1100° C., the substrate temperature was 730° C. at first and 850° C. at the end and was elevated proportionately during this, and the growth time was 5 hours. These WOx nanorods were reduced with methanol at 600° C. under a pressure of $1 \times 10^{-4}$ Torr (process 4). The value x of the WOx nanorods was the same as in Example 1; the length thereof was 3 μm; and the diameter thereof was 30 nm. The WOx nanorods were analyzed for the Raman scattering enhancement degree according to a method of using carbon monoxide. The Raman scattering spectroscopy showed single molecules, and the Raman scattering enhancement degree of the nanorods necessary for observation of single molecules was $1 \times 10^{10}$ or more. The WOx nanorods were analyzed for the applicability thereof to the above-mentioned applications, and it has been confirmed that the nanorods are applicable to all of (1) to (6).

Example 18

WOx nanorods were formed in the same manner as in Example 1, for which, however, the oxygen pressure was $5 \times 10^{-6}$ Torr the heating temperature for the tungsten foil was 1100° C., the substrate temperature was 730° C. at first and 850° C. at the end and was elevated proportionately during this, and the growth time was 5 hours. These WOx nanorods were irradiated with Ar laser (514.5 nm) in air at a narrowed spot diameter of 1 μm and at a relatively high intensity of 1 mW/μm² for local oxidation (process 5). The value x of the WOx nanorods was the same as in Example 1; the length thereof was 3 μm; and the diameter thereof was 30 nm. The WOx nanorods were analyzed for the Raman scattering enhancement degree in the same manner as in Example 17, and the degree was $1 \times 10^{10}$ or more. The WOx nanorods were analyzed for the applicability thereof to the above-mentioned applications, and it has been confirmed that the nanorods are applicable to all of (1) to (6).

Example 19

WOx nanorods were formed in the same manner as in Example 1, for which, however, the oxygen pressure was $5 \times 10^{-6}$ Torr, the heating temperature for the tungsten foil was 1100° C., the substrate temperature was 730° C. at first and 850° C. at the end and was elevated proportionately during this, and the growth time was 5 hours. These WOx nanorods were reduced with CO at room temperature under a pressure of 1 Torr for 3 hours (process 6). The value x of the WOx nanorods was the same as in Example 1; the length thereof was 3 μm; and the diameter thereof was 40 nm. The WOx nanorods were analyzed for the Raman scattering enhancement degree in the same manner as in Example 17, and the degree was $1 \times 10^{10}$ or more. The WOx nanorods were analyzed for the applicability thereof to the above-mentioned applications, and it has been confirmed that the nanorods are applicable to all of (1) to (6).

Example 20

WOx nanorods were formed in the same manner as in Example 1, for which, however, the oxygen pressure was $5 \times 10^{-6}$ Torr the heating temperature for the tungsten foil was 1100° C., the substrate temperature was 730° C. at first and 850° C. at the end and was elevated proportionately during this, and the growth time was 5 hours. These WOx nanorods were not processed as in the above. The value x and the dimension of the WOx nanorods were the same as in Example 1. The WOx nanorods were analyzed for the applicability thereof to the above-mentioned applications, and the same results as in Example 1 were obtained.

Example 21

WOx nanorods were formed in the same manner as in Example 1, for which, however, the oxygen pressure was $5 \times 10^{-6}$ Torr, the heating temperature for the tungsten foil was 1100° C., the substrate temperature was 730° C. at first and 850° C. at the end and was elevated proportionately during this, and the growth time was 5 hours. These WOx nanorods were processed according to the process 5. The value x of the WOx nanorods was the same as in Example 1. The WOx nanorods were analyzed for the Raman scattering enhancement degree in the same manner as in Example 17, and the degree was $1 \times 10^{10}$ or more. The WOx nanorods were analyzed for the applicability thereof to the above-mentioned applications, and it has been confirmed that the nanorods are applicable to all of (1) to (6).

Example 22

WOx nanorods were formed in the same manner as in Example 1, for which, however, the oxygen pressure was $5 \times 10^{-6}$ Torr, the heating temperature for the tungsten foil was 1130° C., the substrate temperature was 730° C. at first and 850° C. at the end and was elevated proportionately during this, and the growth time was 5 hours. These WOx nanorods were not processed as in the above. The value x of the WOx nanorods was the same as in Example 1; the length thereof was 2 μm; and the diameter thereof was 30 nm. The WOx nanorods were analyzed for the applicability thereof to the above-mentioned applications, and the same results as in Example 1 were obtained.

Example 23

WOx nanorods were formed in the same manner as in Example 1, for which, however, the oxygen pressure was $5 \times 10^{-6}$ Torr, the heating temperature for the tungsten foil was 1200° C., the substrate temperature was 730° C. at first and 850° C. at the end and was elevated proportionately during this, and the growth time was 5 hours. These WOx nanorods were not processed as in the above. The value x of the WOx nanorods was the same as in Example 1; the length thereof was 2 μm; and the diameter thereof was 30 nm. The WOx nanorods were analyzed for the applicability thereof to the above-mentioned applications, and the same results as in Example 1 were obtained.

Example 24

WOx nanorods were formed in the same manner as in Example 1, for which, however, the oxygen pressure was $5 \times 10^{-6}$ Torr, the heating temperature for the tungsten foil was 1200° C., the substrate temperature was 730° C. at first and 850° C. at the end and was elevated proportionately during this, and the growth time was 5 hours. These WOx nanorods were processed according to the process 5. The value x of the WOx nanorods was the same as in Example 1; the length thereof was 3 μm; and the diameter thereof was 30 nm. The WOx nanorods were analyzed for the Raman scattering enhancement degree in the same manner as in Example 17,

Example 25

WOx nanorods were formed in the same manner as in Example 1, for which, however, the oxygen pressure was $5\times10^{-6}$ Torr, the heating temperature for the tungsten foil was 1250° C., the substrate temperature was 730° C. at first and 850° C. at the end and was elevated proportionately during this, and the growth time was 5 hours. These WOx nanorods were not processed as in the above. The value x of the WOx nanorods was the same as in Example 1; the length thereof was 4 μm; and the diameter thereof was 40 nm. The WOx nanorods were analyzed for the applicability thereof to the above-mentioned applications, and the same results as in Example 1 were obtained.

Example 26

WOx nanorods were formed in the same manner as in Example 1, for which, however, the oxygen pressure was $5\times10^{-6}$ Torr, the heating temperature for the tungsten foil was 1250° C., the substrate temperature was 730° C. at first and 850° C. at the end and was elevated proportionately during this, and the growth time was 5 hours. These WOx nanorods were processed according to the process 5. The value x of the WOx nanorods was the same as in Example 1; the length thereof was 4 μm; and the diameter thereof was 40 nm. The WOx nanorods were analyzed for the applicability thereof to the above-mentioned applications, and the same results as in Example 1 were obtained.

Example 27

WOx nanorods were formed in the same manner as in Example 1, for which, however, the oxygen pressure was $5\times10^{-6}$ Torr, the heating temperature for the tungsten foil was 1250° C., the substrate temperature was 730° C. at first and 850° C. at the end and was elevated proportionately during this, and the growth time was 5 hours. These WOx nanorods were reduced with carbon adhering to the surfaces thereof through exposure to air, and then annealed in vacuum at 650° C. (process 7). The value x of the WOx nanorods was the same as in Example 1; the length thereof was 4 μm; and the diameter thereof was 40 nm. The WOx nanorods were analyzed for the applicability thereof to the above-mentioned applications, and the same results as in Example 1 were obtained.

Comparative Example 1

The substrate used in Example 1 was directly analyzed for the applicability of the above-mentioned applications, and it has been confirmed that the substrate is not applicable to any of those applications.

The invention claimed is:

1. A probe for Raman scattering spectroscopy, the probe comprising:
   a probe body; and
   an optical electric field enhancement element comprising a tungsten oxide nanorod which includes a plurality of conductive layers formed therein in a direction parallel to a longitudinal axis of the nanorod,
   wherein the conductive layers are comprised of oxygen-deficient planes, and adjacent conductive layers are isolated from each other via an insulating layer,
   wherein the composition of the nanorod is WOx, $2.5 \leq x \leq 3$,
   wherein the optical electric field enhancement element is treated through local oxidation of the tungsten oxide nanorod by laser irradiation in air,
   wherein an active site of enhanced Raman spectroscopy is located at a tip of the nanorod, and
   wherein the optical electric field enhancement element exhibits a Raman scattering enhancement effect of $10^{10}$ and is thereby capable of detecting single-molecule Raman scattering.

2. The probe of claim 1, wherein the nanorod comprises a rod-shaped tungsten oxide crystal having a diameter of 10 to 100 nm and a length of 100 nm to 30 μm.

3. The probe of claim 2, wherein the nanorod has a {001} crystallographic shear structure in the crystal, and has a nano-gap structure in which the conductive layers on an atomic layer level are isolated from each other by the insulating layer.

4. The probe of claim 1, wherein the probe is configured to detect molecules in a thin concentration of at most 1 nM in an aqueous solution using the Raman scattering enhancement effect of the tungsten oxide nanorod.

5. The probe of claim 1, wherein the nanorod is configured to detect molecular vibration of single molecules in an aqueous solution using the Raman scattering enhancement effect of the tungsten oxide nanorod.

6. The probe of claim 1, wherein the probe is configured to reduce a local chemical reaction by exciting molecules existing in the vicinity of the tungsten oxide nanorod by light or heat through photoirradiation of the nanorod.

7. A probe for Raman scattering spectroscopy, the probe comprising:
   a probe body; and
   an optical electric field enhancement element comprising a tungsten oxide nanorod which includes a plurality of conductive layers formed therein in a direction parallel to a longitudinal axis of the nanorod,
   wherein the conductive layers are comprised of oxygen-deficient planes, and adjacent conductive layers are isolated from each other via an insulating layer,
   wherein the composition of the nanorod is WOx, $2.5 \leq x \leq 3$,
   wherein the optical electric field enhancement element is treated through local reduction of the tungsten oxide nanorod by heating in the presence of carbon or carbon monoxide,
   wherein an active site of enhanced Raman spectroscopy is located at a tip of the nanorod, and
   wherein the optical electric field enhancement element exhibits a Raman scattering enhancement effect of $10^{10}$ and is thereby capable of detecting single-molecule Raman scattering.

8. The probe of claim 7, wherein the nanorod comprises a rod-shaped tungsten oxide crystal having a diameter of from 10 to 100 nm and a length of from 100 nm to 30 μm.

9. The probe of claim 8, wherein the nanorod has a {001} crystallographic shear structure in the crystal, and has a nano-gap structure in which the conductive layers on an atomic layer level are isolated from each other by the insulating layer.

10. The probe of claim 7, wherein the probe is configured to detect molecules in a thin concentration of at most 1 nM in an aqueous solution using the Raman scattering enhancement effect of the tungsten oxide nanorod.

11. The probe of claim 7, wherein the nanorod is configured to detect molecular vibration of single molecules in an aqueous solution using the Raman scattering enhancement effect of the tungsten oxide nanorod.

12. The probe of claim 7, wherein the probe is configured to reduce a local chemical reaction by exciting molecules existing in the vicinity of the tungsten oxide nanorod by light or heat through photoirradiation of the nanorod.

\* \* \* \* \*